United States Patent [19]

Vellekamp et al.

[11] Patent Number: 5,328,989
[45] Date of Patent: Jul. 12, 1994

[54] PURIFICATION OF HUMAN INTERLEUKIN-10 FROM A CELL CULTURE MEDIUM

[75] Inventors: Gary Vellekamp, Glen Ridge; Susan Cannon-Carlson, Wayne; John Tang, Livingston, all of N.J.

[73] Assignee: Schering-Plough, Kenilworth, N.J.

[21] Appl. No.: 26,942

[22] Filed: Mar. 5, 1993

[51] Int. Cl.[5] .................. C07K 3/02; C07K 3/20; C07K 3/22; C07K 15/06
[52] U.S. Cl. .................. 530/351; 435/69.52; 435/70.4; 530/415; 530/416
[58] Field of Search .............. 530/412, 351, 415, 416, 530/417; 435/70.1, 70.3, 70.4, 69.52

[56] References Cited

U.S. PATENT DOCUMENTS

| | | | |
|---|---|---|---|
| 4,751,078 | 6/1988 | Nagabhushan et al. | 424/85 |
| 4,855,238 | 8/1989 | Gray et al. | 435/243 |
| 4,929,700 | 5/1990 | Halenbeck et al. | 530/351 |
| 5,055,555 | 10/1991 | Sassenfeld | 530/351 |
| 5,227,302 | 7/1993 | Heldin et al. | 435/240.2 |
| 5,231,012 | 7/1993 | Mosmann et al. | 435/69.52 |

FOREIGN PATENT DOCUMENTS

9100349  1/1991  PCT Int'l Appl. .

OTHER PUBLICATIONS

Guide to Protein Purification Murray Deutscher (Ed) Academic, Press Inc. (1990).
Ingley, et al. "Production & Purification of recombinant human interleukin-S from yeast & baculovhus expression systems". Eur. J. Biochem 196 623-629. 1991.
Mosmann et al "Isolation of Monoclonal Antibodies Specific For 12-4, 12-5, 12-6 and a New ThZ Specific Cytokine (11-10), Cytokine Synthesis Inhibitory Factor, By Using A Solid Phase Radioimmunoadsorbent Assay" J. Immunol. 145: 9 2938-2945 Nov. 1, 1991.

Primary Examiner—Jeffrey E. Russel
Assistant Examiner—Nancy J. Gromet
Attorney, Agent, or Firm—Paul G. Lunn; Norman C. Dulak; Steinar V. Kanstad

[57] ABSTRACT

A method for purifying Interleukin-10 (Il-10) from a eukaryotic cell culture medium. The method is comprised of subjecting IL-10 containing cell culture medium to cation exchange chromatography, anion exchange chromatography, hydroxyapatite chromatography, and gel filtration chromatography. The present invention is also comprised of a process for separating different IL-10 dimers present in a protein fraction from each other by subjecting the protein fraction to hydroxyapatite chromatography. The present invention is also comprised of a process for separating variants of a protein differing in an N-terminal amino acid sequence present in a protein fraction from each other by subjecting the protein fraction to hydroxyapatite chromatography.

17 Claims, No Drawings

PURIFICATION OF HUMAN INTERLEUKIN-10 FROM A CELL CULTURE MEDIUM

BACKGROUND OF THE INVENTION

Interleukin-10 (IL-10), a recently discovered lymphokine, was originally described as an inhibitor of interferon-γ synthesis and is postulated as a major mediator of the humoral class of immune response [Fiorentino, D. F., et al., J. Exp. Med. 170: 2081 (1989) and Moore et al., K. W., et al., Science 248: 1230–1234 (1990)]. Two classes of often mutually exclusive immune responses are the humoral (antibody-mediated) and the delayed-type hypersensitivity.

It is postulated that these two differing immune responses may arise from two types of helper T-cell clones, namely Th1 and Th2 helper T-cells, which demonstrate distinct cytokine secretion patterns [Moore supra; Vieira, P. et al., Proc. Nat. Acad. Sci. USA Vol. 88: 1172 (1991)]. Mouse Th1 cell clones secrete interferon-γ and IL-2 and preferentially induce the delayed-type hypersensitivity response while Th-2 cell clones secrete Il-4, IL-5 and IL-10 and provide support for the humoral responses [Fiorentino et al., supra]. The contrast in immune response could result because interferon-γ secreted by the Th1 cell clones inhibits Th2 clone proliferation in vitro, while IL-10 secreted by the Th2 cell clones inhibit cytokine secretion by the Th1 cell clones [Fiorentino et al., supra and Moore et al., supra]. Thus the two T-helper cell types may be mutually inhibitory and may provide the underpinning for the two dissimilar immune responses.

IL-10 has been cloned and sequenced from both murine and human T cells [Moore et al., supra; Vieira et al., supra]. Both sequences contain an open reading frame encoding a polypeptide of 178 amino acids with an N-terminal hydrophobic leader sequence of 18 amino acids, and have an amino acid sequence homology of 73%.

Biologically active IL-10 is a dimer comprised of non-covalently bonded polypeptides. N-terminal analysis indicates that a small percentage of Il-10 polypeptides have the first two N-terminal amino acid residues missing. This truncated polypeptide is referred to as the Δ2 IL-10 polypeptide, or simple Δ2. The full-length chain is therefore referred to as Δ0, indicating that no amino acid has been deleted. Accordingly, biologically active IL-10 can be expressed as three different dimers. The first biologically active dimer and the major form is Δ0:Δ0, a homodimer in which both polypeptides of the dimer have the full-length chain of amino acids. The second IL-10 dimer is Δ0:Δ2, a heterodimer in which one of the polypeptide chains has the full-length chain of amino acids and the second chain, Δ2, has the first two N-terminal amino acids missing. The third IL-10 dimer is Δ2:Δ2, a homodimer in which both polypeptide chains of the dimer have the initial two N-terminal amino acid residues missing.

In light of its role as a potential immune response mediator and its activity as an inhibitor of interferon-γ synthesis, IL-10 may have clinical utility in autoimmune diseases or transplant rejection. However, in a clinical setting it is highly desirable that the IL-10 be in a highly pure state, substantially free of other contaminating host and medium proteins or polypeptides.

Thus there is a need for purifying IL-10 from culture medium, and in particular there is a need for a method for separating the different dimers of IL-10 from each other.

SUMMARY OF THE INVENTION

The present invention fills this need by providing a process for purifying IL-10 from cell culture medium comprising:

(a) subjecting the culture medium containing IL-10 to cation exchange chromatography thereby obtaining fractions containing Il-10;

(b) subjecting the IL-10-containing fractions from step (a) to anion exchange chromatography thereby obtaining fractions containing ILO10;

(c) subjecting the IL-10-containing fractions from step (b) to hydroxyapatite chromatography thereby obtaining fractions containing a single isolated dimer of IL-10; and (d) subjecting the IL-10-containing fractions from step (c) to gel-filtration chromatography thereby obtaining IL-10 containing fractions free of high and low molecular weight impurities.

The present invention further provides a method for separating different IL-10 dimers contained within a protein fraction containing a mixture of dimers comprising subjecting the fraction to hydroxyapatite chromatography under conditions in which the dimers separate from each other.

The present invention further provides a method for separating different dimers of a protein contained within a protein fraction wherein the different dimers have different N-terminal amino acid sequences comprising subjecting the protein fraction to hydroxyapatite chromatography under conditions wherein the different dimers of the protein are separated from each other.

The present invention further provides a method for separating variants of a protein contained within a protein fraction wherein the variants of the protein have different N-terminal amino acid sequences comprising subjecting the protein fraction to hydroxyapatite chromatography under conditions wherein the variants of the protein are separated from each other.

DESCRIPTION OF THE INVENTION

All references cited herein are hereby incorporated in their entirety by reference.

As used herein, "interleukin-10" or "IL-10" can be either human IL-10 (h IL-10) or murine IL-10. Human IL-10 is defined as a protein which (a) has an amino acid sequence substantially identical to a known sequence of mature (i.e., lacking a secretory leader sequence) hIL-10 as disclosed in U.S. patent application Ser. No. 07/917,806, now U.S. Pat. No. 5,231,012, filed Jul. 20, 1992, which corresponds to International Application No. PCT/US90/03554, Publication No. WO 91/99349, and (b) has biological activity that is common to native hIL-10.

IL-10 can be obtained from culture media of activated T-cells capable of secreting the protein. Preferentially, however, it is obtained by recombinant techniques using isolated nucleic acids encoding for the IL-10 polypeptide. General methods of molecular biology are described, e.g., by Sambrook, et al., *Molecular Cloning, A Laboratory Manual*, Cold Spring Harbor Publish., Cold Spring Harbor, N.Y. 2d ed. 1989 and by Ausubel et al., (eds) *Current Protocols in Molecular Biology*, Green/Wiley, N.Y. (1987 and periodic supplements). The appropriate sequences can be obtained from either genomic or cDNA libraries. Polymerase chain reaction (PCR) techniques can be used. See, e.g., *PCR Protocols: A Guide to Methods and Applications*, 1990, Innis et al., (Ed.), Academic Press, New York, N.Y.

Libraries are constructed from nucleic acid extracted from appropriate cells. See, for example, International Application Publication No. WO 91/00349, which discloses recombinant methods to make IL-10. Useful gene sequences can be found, e.g., in various sequence data bases, e.g., Gen Bank and EMBL for nucleic acid, and PIR and Swiss-Prot for protein, c/o Intelligenetics, Mountain View, Calif., or the Genetics Computer Group, University of Wisconsin Biotechnology Center, Madison, Wis., which are incorporated herein by reference.

Clones comprising sequences that encode human IL-10 (hIL-10) have been deposited with the American Type Culture Collection (ATCC), Rockville, Md., under Accession Numbers 68191 and 68192. Identification of other clones harboring the sequences encoding IL-10 is performed by either nuclei acid hybridization or immunological detection of the encoded protein, if an expression vector is used. Oligonucleotide probes based on the deposited sequences are disclosed in International Application Publication No. WO 91/00349. Oligonucleotide probes useful for identification of the sequences can also be prepared from conserved regions of related genes in other species. Alternatively, degenerate probes based on the amino acid sequence of IL-10 can be used.

Various expression vectors can be used to express DNA encoding IL-10. Conventional vectors used for expression of recombinant proteins used for expression of recombinant proteins in prokaryotic or eukaryotic cells may be used. Preferred vectors include the pcD vectors described by Okayama et al., *Mol. Cell. Bio.* Vol. 3: 280–289 (1983); and Takebe et al., *Mol. Cell. Biol.* Vol. 8: 466–472 (1988). Other SV40-based mammalian expression vectors include those disclosed in Kaufman et al., *Mol. Cell. Biol.* Vol. 2: 1304–1319 (1982) and U.S. Pat. No. 4,675,285. These SV40-based vectors are particularly useful in COS7 monkey cells (ATCC No. CRL 1651), as well as in other mammalian cells such as mouse L cells and CHO cells.

Standard transfection methods can be used to produce eukaryotic cell lines which express large quantities of the polypeptide. The process of the present invention is a process to purify IL-10 expressed by eukaryotic cells from a cell supernatant into which the protein was expressed. Eukaryotic cell lines include mammalian, yeast and insect cell lines. Exemplary mammalian cell lines include COS-7 cells, mouse L cells and Chinese Hamster Ovary (CHO) cells. See Sambrook et al., supra and Ausubel et al., supra.

The method of the present invention comprises the sequential application of cation-exchange, anion-exchange, hydroxyapatite and gel-filtration chromatography. To achieve high purity and maximal yield, each of the four chromatographic steps were selected and optimized in regards to pH, conductivity, buffer composition, flow rates and column dimensions. The analytic procedures utilized to determine this optimization of purity and yield were Western blots, sodium dodecyl sulfate-polyacrylamide gel electrophoresis (SDS-PAGE) Laemmli, U.K., Nature 227:680 (1970), Enzyme-Linked Immunoadsorbant Assay (ELISA) values, UV absorbance at 280 and 260 nm and protein concentration determinations [(Bardford, M. Anal. Biochem., 72: 248 (1976)].

Furthermore, the order of chromatographic steps were optimized for efficient and rapid large-scale processing as well as product purity and yield. This includes 1) product concentration during the first step (cation exchange) to reduce volume handling; 2) a flow-through mode for the second step (anion exchange) such that the product of this fast step can immediately be loaded on the next column without extra processing; 3) the removal of almost all contaminating proteins during the first two steps so that there is no interference by these other proteins with the resolution of the IL-10 forms on the third column (hydroxyapatite) and 4) besides separation of trace contaminants of differing molecular weights and IL-10 monomer, the buffer exchange of the gel filtration chromatography allows the final product IL-10 to be obtained in a buffer desired for further pharmaceutical formulation.

The cation exchange chromatography step is used first because IL-10 adsorbs well to a cation exchange resin. Any cationic exchange group can be used such as carboxymethyl, sulfopropyl and sulfonate. The cationic exchange group can be attached to any solid-phase support including but not limited to cellulose, dextrans, agarose and polystyrene. The preferred cation exchange group is sulfonate attached to an agarose packing support matrix, such an S-SEPHAROSE Fast Flow ® from (Pharmacia, Piscataway, N.J.). The equilibrating buffer should be at a pH lower than 7.8, the pI of IL-10, and preferably about 6.5 for S-SEPHAROSE, in order to create sufficient positive charges on the IL-10 protein. This creates good adhesion of the IL-10 protein to the cationic exchange group. Conditions are optimized such that 80–90% of contaminant proteins, and especially serum albumin, the major contaminant protein, are not bound. The amount of protein that is to be loaded can be determined experimentally based upon information provided by the manufacturer. Using a 5×28 cm S-SEPHAROSE ® Fast Flow column, approximately 100 mg protein/ml of bed volume can be applied at a flow rate of 1.1 cm/min. After the supernatant is loaded, the column is developed with either a step or linear gradient salt solution, preferably a 70–300 mM NaCl linear gradient for an S-SERHAROSE ® column. IL-10 elutes at a concentration of about 150 mM NaCl at a distinct peak of $A_{280}$ at approximately 17 mS. Ideally IL-10 containing fractions are then concentrated and diafiltered by, for example, using a PELLICON ®, 10K membrane.

The IL-10-containing fractions from the cation exchange chromatography are subjected to anion exchange chromatography which substantially removes the remaining cell culture protein contaminants. Any anionic exchange group can be used. Examples are quarternary aminoethyl, mixed amine or other intermediate base or weak base exchange groups. Quarternary aminoethyl is a preferred anion exchange group. The quarternary aminoethyl group may be attached to a dextran, cellulose, agarose or acrylic support matrix. Preferably the support is agarose. An ideal QAE agarose anion exchange resin is Q-SEPHAROSE ® (Pharmacia, Piscataway, N.J.). IL-10 does not adsorb to a QAE anion exchange resin at the optimal pH of 8.0–8.3. Thus, IL-10 passes through a QAE column while most contaminating proteins are absorbed if the mg protein/ml bed volume is below 4.

The IL-10-containing protein fractions obtained from the anion exchange column are subjected to hydroxyapatite chromatography in order to separate the different dimeric forms of IL-10 present in the fractions. This can be done by a fast flow method in which the anion exchange column is placed directly above the hydroxyapatite column so that the fractions from the anion exchange column are immediately loaded onto the hydroxyapatite column as they come off of the anion exchange column. The hydroxyapatite column is equilibrated with a standard salt solution at a pH of about 8.1. A suitable buffer for this purpose is comprised of 20 mM Tris-Cl, and 20 mM NaCl, pH 8.1. The IL-10 containing fractions are loaded onto the hydroxyapatite column and eulted preferably with a 20 bed volume linear gradient of a 150 mM potassium phosphate buffer at about a pH of 8.0. The elution is started with about a 6% concentration of the $KPO_4$ buffer and increases gradually until a concentration of about 75% is reached. $NaPO_4$ can also be used at the same concentration levels. The $\Delta 0:\Delta 0$ IL-10 dimer elutes off at about a 20-25% concentration of the 150 mM $KPO_4$ buffer. The other two dimers elute off at about 30-35% of the 150 mM $KPO_4$ buffer. $\Delta 0:\Delta 2$ can be separated from $\Delta 2:\Delta 2$ preferably by doubling the length of the column and applying and reapplying the resultant fractions until the $\Delta 0:\Delta 2$ and the $\Delta 2:\Delta 2$ come out in separate fractions.

Using hydroxyapatite chromatography, different IL-10 dimers present together in IL-10-containing fractions can be separated from each other. The fact that the different dimers have indeed been separated can be determined by N-terminal amino acid residue sequence analysis.

The isolated IL-10-dimer-containing fractions obtained from the hydroxyapatite column are then subjected to gel filtration. Gel filtration is used to separate high and low molecular weight impurities including IL-10 monomer. Two particularly useful gels are SEPHACRYL S-200 HR ® which has a fractionation range of from 5 kDa to about 250 kDa for proteins, and SEPHACRYL S-100 ®, which has a fractionation range of from 1 to 100 kDa for proteins. Other gels which have fractionation ranges from about 1 kDa to 600 kDa for proteins may also be used.

Variant forms of a protein differing in the N-terminal amino acid sequence can be separated using hydroxyapatite chromatography. A protein, monomeric or oligomeric, may be purified but still retain heterogeneity due to variants missing one or more N-terminal amino acids. These variants may be separated by hydroxyapatite chromatography. In order to effect these separations a number of experimental variables are examined. First is the phosphate concentration necessary to elute and the gradient of the phosphate concentration. Secondary variable to be examined are the column length, protein loading, pH, net conductivity and low levels of divalent cations. Rechromatography under somewhat altered conditions is likely to improve the yield and purity of the variant forms.

The following example is included to illustrate but not limit the present invention.

EXAMPLE

Purification of Human IL-10 from CHO-Cell Line Culture Medium

Chinese Hamster Ovary (CHO) cells were transfected with a vector containing the IL-10 gene and were grown in Iscove's Modified Dulbecco's Medium (IMDM) a basal medium containing salts, buffers, vitamins, amino acids, and glucose (Sigma, St. Louis, Mo.) supplemented with 5% NUSERUM V ® a medium supplement containing 25% newborn calf serum, hormones growth factors and other nutrients (Collaborative Research) and HBCHO ® a serum-free supplement containing bovine serum albumin, insulin, transferrin, fetuin, fatty acids, ethanolamine, and selenium (Irvine Scientific). The transfected CHO cells were grown in the cell medium at 37° C. at a pH of 7.2. After five days of growth, a total of 177 liters of the cell culture supernatant liquid was drawn off, subjected to crossflow microfiltration and concentrated to about 17.6 liters by ultrafiltration. The CHO-cell culture supernatant was then diafiltered with 20 mM MES (2-[N-Morpholino]ethanesulfonic acid), 65 mM NaCl, pH 4. The resultant supernatant liquid was then subjected to the following chromatographic procedures, all of which were performed at 4° C.

Cation—Exchange Chromatography

The concentrated, diafiltered CHO-cell supernatant concentrate was loaded on a 5×28 cm S-SEPHAROSE ™ Fast Flow column equilibrated with 20 mM MES, 70 mM NaCl pH 6.5. Approximately 100 mg protein/ml of bed volume was applied at a flow rate of 1.1 cm/min. The column was washed with 8.5 bed volumes of equilibration buffer. This was followed by elution with a 13 bed volume, 70-300 mM NaCl gradient at a reduced flow rate of 0.6 cm/min. The hIL-10 eluted at a distinct peak of $A_{280}$ at approximately 17 mS which corresponded to about 150 mM NaCl and it was the major protein eluted at 16-10 mS. The fractions containing hIL-10 were concentrated and diafiltered (PELLICON ®, 10K membrane) with Buffer A, which was comprised of 20 mM Tris-Cl, 20 mM NaCl, pH 8.1.

Cation-exchange chromatography utilizing S-SEPHAROSE ® produced good adsorption and was therefore chosen as the first purification step. Using the conditions described above, 80–90% of the contaminant protein was not bound. Although hIL-10 was 1% of the initial protein, it was the major protein eluted at 16–20 mS and was purified 50-fold. See Table 1 below. Optimal conditions of pH, conductivity, flow rates, and column dimensions were determined by evaluating UV absorbance at 280 and 260 nm, protein concentration, ELISA values, SDS-PAGE, and Western blot results of numerous chromatographies.

Anion-Exchange Chromatography

The concentrated, diafiltered, IL-10-containing fractions obtained from the cation-exchange chromatography step were loaded on a 5×13 cm Q-SEPHAROSE ® Fast Flow column equilibrated with Buffer A. The protein loading was approximately 3.5 mg/ml bed volume at 0.5 cm/min. The column was then washed with the Buffer A until the absorbance at $A_{280}$ was minimal. The protein which did not adsorb to the Q-SEPHAROSE ® contained the hIL-10 and was pooled for direct loading onto hydroxyapatite.

Human IL-10 had little affinity for various anion exchange columns, showing minimal binding at pHs up to 8.1, and conductivities down to 4 mS. This allowed Q-SEPHAROSE ® chromatography in the flow-through mode where hIL-10 passed directly through the column, while most contaminating proteins were absorbed if the mg protein/ml bed volume was kept below 4. Since there is no buffer adjustment of the Q-SEPHAROSE ™ pool prior to hydroxyapatite chromatography, the two columns can be connected in tandem so that the effluent of the Q-SEPHAROSE ® column is loaded directly on the hydroxyapatite column.

Hydroxyapatite Chromatography

The IL-10 containing fractions obtained from the Q-SEPHAROSE ® column were loaded on a 2.6×26 cm hydroxyapatite column and equilibrated with Buffer A in order to separate the IL-10 dimers which were present in the fractions. The hydroxyapatite which was used was ceramic hydroxyapatite from Pentax and distributed by American International Chemical Inc. Ceramic hydroxyapatite is formed by heating i.e., sintering, the hydroxyapatite crystals into beads. Standard, i.e., non-sintered, hydroxyapatite (Biorad) is also acceptable. The protein loading was at approximately 2.5 mg/ml bed volume at a flow rate of 0.6 cm/min. The column was washed with 5 bed volumes of a mixture of 94% Buffer A and 6% Buffer B. Buffer B was comprised of 150 mM $KPO_4$, pH 8.0. The Il-10 was eluted with a linear gradient from 6% of Buffer B. The $\Delta 0:\Delta 0$ dimer eluted out at approximately 20–25% concentration of Buffer B. The $\Delta 0:\Delta 2$ and the $\Delta 2:\Delta 2$ dimers eluted out at approximately 30–35% concentration of Buffer B.

Gel-Filtration Chromatography

Separate concentrated hydroxyapatite pools containing the $\Delta 0:\Delta 0$ IL-10 dimer (up to ~20 mg/ml) were loaded onto either a SEPHACRYL ® S-200 HR or SEPHACRYL ® S-100 HR column (2.6×85 cm) equilibrated and eluted with Buffer C which was comprised of 20 mM Tris-Cl, 150 mM NaCl, pH 8.1. The sample loading volume was less than 4% of the bed volume and the flow rate was 0.1 cm/min. Peak fractions were pooled and stored at −20° C.

Gel filtration chromatography in either SEPHACRYL ® S-200 HR or SEPHACRYL ® S-100 HR revealed that hIL-10 displayed a molecular weight consistent with a dimeric form. The $\Delta 0:\Delta 0$ dimer was the predominant form for all protein concentrations loaded (0.2–20 mg/ml of bed volume). Small amounts (<5%) of hIL-10 monomer were occasionally seen as a trailing shoulder on a $A_{280}$ profile, and these fractions were excluded from the pool.

The overall purification procedure yielded approximately 1.1 mg of at least 98% pure $\Delta 0:\Delta 0$ human IL-10 per liter of cell culture medium. Purity was determined by sodium dodecyl sulfate-polyacrylamide gel electrophoresis (SDS-PAGE), Laemmli, U.K., *Nature*, 227: 680 (1970). In addition, HPLC chromatography with either reversed-phase (C4) or with size exclusion ZORBEX ® 250 showed only a single peak. The performance of each of the purification steps is shown in the following Table, in which results are an average from three purification runs of approximately 175 liters each of CHO cell supernatant (containing 5% Nu-Serum V).

TABLE 1

Purification of CHO hIL-10

| Step | Absorbance ($A_{280}$ units) | Total Proteins (mg) | hIL-10[a] (mg) | Yield[a] (%) | Purity[b] (%) |
|---|---|---|---|---|---|
| cell culture | 55,000 | 57,000 | 600 | 100 | 1.1 |
| S-Sepharose | 680 | 890 | 430 | 72 | 48 |
| Q-Sepharose | 190 | 360 | 290 | 48 | 81 |
| Hydroxyapatite | 130 | 200 | 210 | 35 | 92 |
| Sephacryl S-200 | 73 | 180 | 200 | 33 | 98 |

[a] Concentration and yield of hIL-10 was based on an ELISA assay.
[b] Purity was determined as mg hIL-10 (as determined by ELISA)/mg total protein (as determined by the Bradford Assay supra) × 100 for the cell culture concentrate, S-Sepharose pool, and Q-Sepharose pool. Purity was determined from SDS-PAGE by comparison of band intensity at varying protein amounts for the hydroxyapatite pool and the Sephacryl S-200 pool. In this technique known amount of the sample ranging from 0.005–25 μg were run in different lanes of an SDS-PAGE gel. The relative amount of contaminants seen at high loading were determine by comparison with the band intensity of IL-10 seen at low loadings.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention, which is only to be limited by the claims.

What is claimed is:

1. A method for purifying Interleukin-10 (IL-10) from a cell culture medium comprising:
    (a) subjecting the culture medium containing IL-10 to cation exchange chromatography thereby obtaining fractions containing IL-10;
    (b) subjecting the IL-10-containing fractions from step (a) to anion exchange chromatography thereby obtaining fractions containing IL-10;
    (c) subjecting the IL-10-containing fractions from step (b) to hydroxyapatite chromatography thereby obtaining fractions containing a single isolated dimer of IL-10.

2. The method of claim 1 wherein the cation exchange chromatography from step (a) uses a column comprised of sulfonate exchange groups attached to a support matrix.

3. The method of claim 2 wherein the support matrix is agarose.

4. The method of claim 1 wherein the anion exchange chromatography uses a column comprised of quartenary amino ethyl exchange groups attached to a support matrix.

5. The method of claim 4 wherein the support matrix is agarose.

6. The method of claim 1 further comprising applying the IL-10-containing fractions obtained from step (c) of claim 1 to a gel filtration chromatography column to obtain dimeric IL-10 substantially free of high and low molecular weight impurities.

7. The method of claim 6 wherein the gel has a fractionation range of from 1 to 600 kDa.

8. The method of claim 1 wherein the IL-10 is human IL-10.

9. The method of claim 1 wherein IL-10 is secreted in a cell culture medium from eukaryotic cell.

10. A method for separating different dimers of IL-10 present in an IL-10 containing protein fraction comprising:
    subjecting the IL-10 containing fraction to hydroxyapatite chromatography under conditions wherein the different IL-10 dimers are separated from each other.

11. The method of claim 10 wherein the IL-10 dimers present in the protein fraction are Δ0:Δ0, Δ0:Δ2 and Δ2:Δ2 IL-10 dimers.

12. The method of claim 11 wherein the IL-10 dimer which is collected is the Δ0:Δ0 IL-10 dimer.

13. The method of claim 11 wherein the IL-10 dimer which is collected is the Δ0:Δ2 IL-10 dimer.

14. The method of claim 11 wherein the IL-10 dimer which is collected is the Δ2:Δ2 IL-10 dimer.

15. The method of claim 10 wherein the hydroxyapatite is sintered hydroxyapatite.

16. A method for separating different dimers of a protein contained within a protein fraction wherein the different dimers have different N-terminal amino acid sequences comprising:
subjecting the protein fraction to hydroxyapatite chromatography under conditions wherein the different dimers of the protein are separated from each other.

17. A method for separating variants of a protein contained within a protein fraction wherein the variants of the protein have different N-terminal amino acid sequences comprising:
subjecting the protein fraction to hydroxyapatite chromatography under conditions wherein the variants of the protein are separated from each other.

* * * * *